United States Patent [19]

Jendralla et al.

[11] Patent Number: 4,946,852
[45] Date of Patent: Aug. 7, 1990

[54] 4(R)-SUBSTITUTED 6(S)-PHENOXYMETHYL-, 6(S)-BETA-PHENYLENTHYL-AND 6(S)-BETA-STYRYL-TETRAHYDROPYRAN-2-ONES, A HIGHLY STEREOSELECTIVE PROCESS FOR THEIR PREPARATION, PHARMACEUTICAL PRODUCTS BASED ON THESE COMPOUNDS, AND THEIR USE

[75] Inventors: Heiner Jendralla, Kelkheim; Gerhard Beck, Frankfurt am Main; Günther Wess, Erlensee; Bela Kerekjarto, Hofheim am Taunus, all of Fed. Rep. of Germany

[73] Assignee: Hoechst Aktiengesellschaft, Frankfurt am Main, Fed. Rep. of Germany

[21] Appl. No.: 330,979

[22] Filed: Mar. 30, 1989

Related U.S. Application Data

[63] Continuation of Ser. No. 46,689, May 7, 1987, abandoned.

[30] Foreign Application Priority Data

May 9, 1986 [DE] Fed. Rep. of Germany ....... 3615620

[51] Int. Cl.$^5$ .................. A61K 31/365; A61K 31/44; C07B 213/24; C07B 307/08
[52] U.S. Cl. .................................... 514/336; 514/444; 514/449; 514/459; 514/460; 514/824; 549/292; 549/293; 549/60; 546/340; 546/342
[58] Field of Search ............... 549/292, 293, 263, 273, 549/60; 514/460, 449, 444, 336, 459, 824; 546/340, 342

[56] References Cited

U.S. PATENT DOCUMENTS

| | | | |
|---|---|---|---|
| 4,255,444 | 3/1981 | Oka et al. | 514/460 |
| 4,440,927 | 4/1984 | Prugh | 549/292 |
| 4,661,483 | 4/1987 | Hoffman et al. | 514/459 |
| 4,710,513 | 12/1987 | Willard et al. | 549/292 |

FOREIGN PATENT DOCUMENTS 164049 12/1985 European Pat. Off. ............ 549/292

| | | | |
|---|---|---|---|
| 2134094 | 1/1972 | Fed. Rep. of Germany | 549/292 |
| 2822848 | 11/1978 | Fed. Rep. of Germany | 549/292 |

OTHER PUBLICATIONS

Bartmann et al., "Convenient Two-Step, etc." TL 27 4709.
Yang et al., "Mevinic Acids and Analogues, etc." TL 23 4305.
Japanese Abstract No. 57-7480.
Japanese Abstract No. 56-5474.
Stokker et al., J. Med. Chem., vol. 28, 1985, pp. 347-358.
Hoffman et al., J. Med. Chem., vol. 29, 1986, pp. 159-180.
A. Endo, J. Med. Chem., vol. 28, 1985, pp. 401-405.
Stokker et al., Journal of Medicinal Chemistry, vol. 29, 1986, pp. 170-181.
Hoffman et al., Journal of Medicinal Chemistry, vol. 29, No. 2, 1985, pp. 159-169.

Primary Examiner—Mark W. Russell
Attorney, Agent, or Firm—Finnegan, Henderson, Farabow, Garrett and Dunner

[57] ABSTRACT

4(R)-Substituted 6(S)-phenyloxymethyl-, 6(S)-$\beta$-phenylethyl- and 6(S)-$\beta$-styryl-tetrahydropyran-2-ones of the general formula V

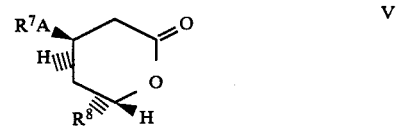

in which $R^7$, $R^8$ and A have the meanings given, and the corresponding open-chain hydroxycarboxylic acids, pharmacologically acceptable salts and esters thereof, processes for the preparation of these compounds, their use as medicaments and pharmaceutical products are described. Novel $\alpha,\beta$-unsaturated lactones for the preparation of the compounds of the formula V are also described.

5 Claims, No Drawings

4(R)-SUBSTITUTED 6(S)-PHENOXYMETHYL-, 6(S)-BETA-PHENYLENTHYL-AND 6(S)-BETA-STYRYL-TETRAHYDROPYRAN-2-ONES, A HIGHLY STEREOSELECTIVE PROCESS FOR THEIR PREPARATION, PHARMACEUTICAL PRODUCTS BASED ON THESE COMPOUNDS, AND THEIR USE

This application is a continuation of application Ser. No. 07/046,689 filed May 7, 1987, now abandoned.

It is known that the enzyme 3-hydroxy-3-methyl-glutarylcoenzyme A reductase (HMG-CoA reductase) catalyzes the formation of mevalonic acid from 3-hydroxy-3-methyl-glutaryl-coenzyme A (HMG-CoA). This reaction plays a central role in the biosynthesis of cholesterol. Derivatives of 3-hydroxy-3-methyl-glutaric acid (HMG) and mevalonic acid have been described in several instances as inhibitors of cholesterol biosynthesis.

G. E. Stokker et al. (J. Med. Chem. 28, 347–358 (1985)) thus describe 5-substituted 3,5-dihydroxypentanoic acid derivatives and 4-hydroxy-lactones thereof and W. F. Hoffmann et al. (J. Med. Chem. 29, 159 et seq. (1986)) describe 7-aryl-substituted 3,5-dihydroxy-6-heptanoic acid derivatives and 4-hydroxy-lactones thereof, which inhibit HMG-CoA reductase.

It has already been proposed (compare German Patent Applications P 35 30 798.6 and P 35 43 336.1 (corresponding to U.S. patent application Ser. No. 900,848) and P 35 30 797.8 (corresponding to U.S. patent application Ser. No. 900,887)) that 6-phenoxymethyl-4-hydroxytetrahydropyran-2-ones and 6(S)-β-phenylethyl and 6(S)-β-styryltetrahydropyran-2-ones of the general formulae given therein and the corresponding dihydroxycarboxylic acids and salts and esters thereof are inhibitors of HMG-CoA reductase and can therefore be used as medicaments, in particular for the prophylaxis and therapy of hypercholesterolaemia.

The compounds which inhibit HMG-CoA reductase and are described in the publications and applications mentioned have an unchanged 4(R)-hydroxyl group in the case of the lactones and 3(R)-hydroxyl group in the case of the dihydroxycarboxylic acids.

The few examples of a change or a replacement of these hydroxyl groups: 4(S)-configuration (G. E. Stokker et al., J. Med. Chem. 28, 347 (1985)), enol grouping or methyl group (G. E. Stokker et al., J. Med. Chem. 28, 347 (1985)) or acetylation (A. Endo, J. Med. Chem. 28, 401 (1985)) had the effect, according to the statements in the literature, of only an extremely slight inhibition of HMG-CoA reductase, if at all.

It has now been found that compounds corresponding to German Patent Applications P 35 30 798.6 and P 35 43 336.1 (=U.S. patent application Ser. No. 900,848) and P 35 30 497.8 (=U.S. patent application Ser. No. 900,887) which carry the radical $R^7$—A— instead of the 4(R)- or 3(R)-hydroxyl group also inhibit HMG-CoA reductase and can therefore be used as medicaments, in particular for the prophylaxis and therapy of hypercholesterolaemia.

The invention therefore relates to tetrahydropyranones of the general formula V

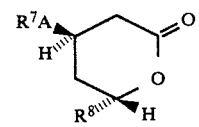

in which:

A denotes —S—, —NH—, $NR^7$ or —$CHR^7$—
$R^7$
(a) denotes a straight-chain or branched alkyl radical which has 1–3 carbon atoms and can be substituted
(aa) by a hydroxyl group
(ab) by an amino or ammonium group
(ac) by a carboxyl group $CO_2H$ or the methyl, ethyl or benzyl ester or methyl- or dimethylamide or sodium, potassium or ammonium salt thereof
(ad) by a phenyl radical
(ae) by 1 to 3 halogen atoms
(b) denotes an alkanoyl group

in which $R^9$ is a straight-chain or branched alkyl radical which has 1 to 4 carbon atoms and can be substituted by the groups mentioned under (aa) to (ae)
(c) denotes a carboxyl group, the methyl, ethyl or benzyl ester, or methyl- or dimethylamide, or sodium, potassium or ammonium salt thereof, or
(d) denotes hydrogen
$R^8$ denotes the structural elements of the formulae VI or VII

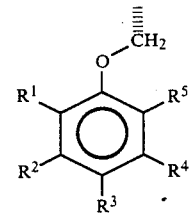

or

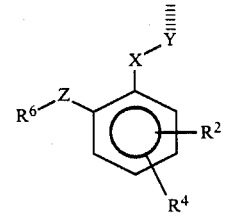

in which
X-Y denotes a radical of the formula trans —CH=CH— or —$CH_2$—$CH_2$—
Z denotes a —$CH_2$— or —$CH_2$—$CH_2$— group
$R^1$ and $R^5$ are identical or different and
(a) denote hydrogen or halogen
(b) denote cycloalkyl with 4 to 8 carbon atoms or a phenyl radical, which can be mono-, di- or trisubstituted in the nucleus by halogen, trifluoromethyl and/or alkyl or alkoxy with in each case 1 to 4 carbon atoms, or (c) denote a straight-chain or branched alkyl radical with 1 to 18 carbon atoms or a straight-chain or branched alkenyl radical with 2 to 18 carbon atoms, it being possible for the alkyl and alkenyl radicals in turn to be mono-, di- or trisubstituted by ($\alpha$) straight-chain or branched alkoxy radicals with up to 10 carbon atoms or cycloalkoxy radicals with 3 to 7 carbon atoms or straight-chain or branched alkenyloxy or alkynyloxy radicals with 3 to 6 carbon atoms, ($\beta$) halogen, hydroxyl, cycloalkyl with 3 to 7 carbon atoms, unsubstituted phenyl or $\alpha$- or $\beta$-thienyl radicals, or phenyl or $\alpha$- or $\beta$-thienyl radicals which are in turn mono-, di- or trisubstituted in the nucleus by halogen, trifluoromethyl and/or alkyl or alkoxy with 1 to 4 carbon atoms, ($\gamma$) unsubstituted phenoxy, benzyloxy or $\alpha$- or $\beta$ thienyloxy radicals, or phenoxy, benzyloxy or $\alpha$- or $\beta$-thienyloxy radicals which are in turn mono-, di- or trisubstituted in the nucleus by halogen, trifluoromethyl and/or alkyl or alkoxy with 1 to 4 carbon atoms, ($\delta$) the group $$-\overset{O}{\underset{\|}{C}}-R^{10},$$

in which $R^{10}$ denotes: a straight-chain or branched alkyl or alkenyl radical with up to 8 carbon atoms, or a cycloalkyl or cycloalkenyl radical with in each case 3 to 8 carbon atoms, or an unsubstituted phenyl radical or a phenyl radical which is in turn mono-, di- or trisubstituted in the nucleus by halogen, trifluoromethyl and/or alkyl or alkoxy with 1 to 4 carbon atoms, or a pyridyl radical, $R^2$ and $R^4$ are identical or different and denote hydrogen, alkyl with 1 to 4 carbon atoms, halogen or alkoxy with 1 to 4 carbon atoms, and $R^3$ denotes hydrogen, alkyl or alkenyl with up to 4 carbon atoms, halogen or alkoxy with 1 to 4 carbon atoms, and $R^6$ denotes a cycloaliphatic hydrocarbon radical with 3 to 7 carbon atoms, a phenyl radical which can be mono-, di- or trisubstituted in the nucleus by halogen, trifluoromethyl, alkyl or alkoxy with in each case 1 to 6 carbon atoms or hydroxymethyl, or a furyl, thienyl or pyridyl radical, it being possible for the heteroaromatic radicals to be mono- or disubstituted by halogen, trifluoromethyl or alkyl or alkoxy with in each case 1 to 6 carbon atoms, and the corresponding open-chain hydroxycarboxylic acids of the formula V'

$$R^{7}A\underset{H}{\overset{\text{......}}{\diagdown}}\diagup\diagdown\diagup^{\text{COOH}}\underset{R^{8}\overset{\text{......}}{\diagdown}H}{\diagdown}\diagup^{\text{OH}}\quad V'$$

in which A, $R^7$ and $R^8$ have the meanings given in the case of formula V, pharmacologically acceptable salts thereof with bases and pharmacologically acceptable esters thereof.

The invention preferably relates to compounds of the general formula V or V' in which:

A denotes —S—

$R^7$ (a) denotes a straight-chain or branched alkyl radical which has 1 or 2 carbon atoms and can be substituted by
 (aa) a hydroxyl group
 (ab) an amino or ammonium group
 (ac) a carboxyl group, or the methyl, ethyl or benzyl ester, or methyl- or dimethylamide, or sodium, potassium or ammonium salt thereof
 (ad) a phenyl radical
 (ae) a fluorine or chlorine atom (b) denotes an alkanoyl group $$R^{9}-\overset{O}{\underset{\|}{C}}-,$$

in which $R^9$ is a methyl or ethyl radical which can be substituted by one hydroxyl group or 1 to 3 fluorine atoms (c) denotes a carboxyl group, or the methyl or ethyl ester, or methyl- or dimethylamide, or sodium, potassium or ammonium salt thereof, or (d) denotes hydrogen $R^8$ denotes the structural elements of the formulae VI or VII

VI or

VII in which

X-Y represents a radical of the formula trans —CH=CH—, and

Z represents a $CH_2$ group, $R^1$ and $R^5$ are identical or different and
 (a) represent hydrogen or chlorine, or
 (b) represent a straight-chain or branched alkyl radical with 1 to 6 carbon atoms, it being possible for the alkyl radical in turn to be mono- or disubstituted by phenyl or phenoxy radicals, which can in turn be substituted in the nucleus by fluorine or chlorine, $R^2$ and $R^4$ are identical or different and are hydrogen, methyl, ethyl, fluorine or chlorine, $R^3$ represents hydrogen, methyl or chlorine and $R^6$ represents a cycloaliphatic hydrocarbon radical with 5 to 6 carbon atoms or a phenyl radical which can be substituted in the nucleus by fluorine, chlorine, trifluoromethyl, methyl, ethyl, methoxy or ethoxy.

The invention particularly preferably relates to compounds of the general formula V or V', in which
A denotes —S—
R⁷
  (a) denotes an alkyl radical which has 1 or 2 carbon atoms and can be substituted by
    (aa) a hydroxyl group
    (ab) an amino or ammonium group
    (ac) a carboxyl group, or the methyl ester, or sodium, potassium or ammonium salt thereof
    (ad) a phenyl radical
    (ae) a fluorine atom, or
  (b) denotes an acetyl or trifluoroacetyl group
R⁸ denotes the structural elements of the formulae VI or VII

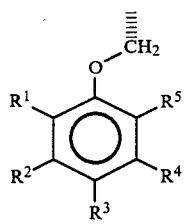

VI or

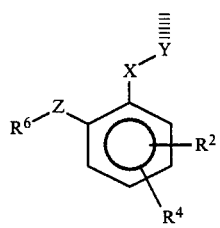

VII in which
X-Y is a radical of the formula trans —CH=CH— and Z is a —CH₂— group,
$R^1$ and $R^5$ are identical or different and
  (a) are chlorine, or
  (b) are a straight-chain or branched alkyl radical with 1 to 3 carbon atoms, it being possible for the alkyl radical in turn to be mono- or disubstituted by phenyl or phenoxy radicals, which can in turn be substituted in the nucleus by fluorine, and
$R^2$ and $R^4$ are hydrogen
$R^3$ is chlorine or methyl and
$R^6$ is cyclohexyl, an unsubstituted phenyl radical or a phenyl radical which is substituted by chlorine or fluorine.

The invention furthermore relates to a process for the preparation of compounds of the formula V and V' and of pharmacologically acceptable salts thereof with bases and pharmacologically acceptable esters thereof, and to the use of corresponding compounds for the prophylaxis and therapy of arteriosclerosis and hypercholesterolaemia, and to pharmaceutical products containing the corresponding compounds.

The process for the preparation of the compounds of the formula V and V' comprises
  (a) reacting compounds of the general formula I or II

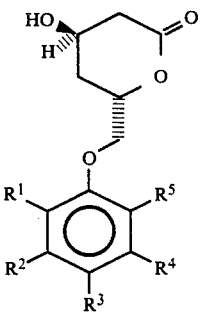

I

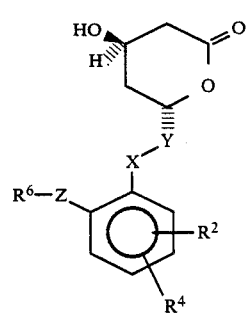

II in which $R^1$, $R^2$, $R^3$, $R^4$, $R^5$, $R^6$, X, Y and Z have the meaning given in the case of formula V, with a dehydrating reagent, for example with Burgess reagent (E. M. Burgess et al., J. Org. Chem. 38, 26 (1973)) to give the α,β-unsaturated lactones of the general formula III or IV

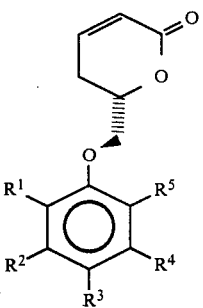

III

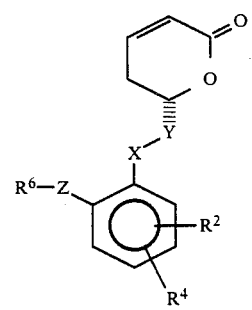

IV or converting the precursors of the formulae I' and II'

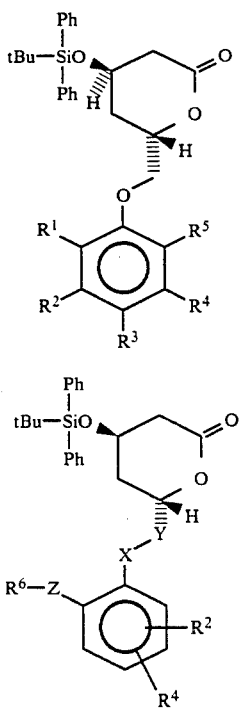

I'

II' in which $R^1$ to $R^6$, X, Y and Z have the meanings given in the case of formula V, into the α,β-unsaturated lactones of the formula III or IV by desiloxylation and (b) reacting the α,β-unsaturated lactones of the formula III or IV with nucleophilic compounds $R^7AH$, such as, for example, $R^7$-substituted mercaptans, thiol acids, amines or C-H-acid compounds, to give compounds of the formula V in which $R^7$ and A have the meanings given in the case of formula V and $R^8$ denotes the structural element VI, in which $R^1$ to $R^5$ have the meanings given, or the structural element VII, in which $R^2$, $R^4$ and $R^6$ have the meanings given and X-Y represents the trans CH=CH group, and if appropriate, hydrogenating a resulting compound V, in which X-Y represents the trans CH=CH group, to give a compound V in which X-Y represents the $CH_2$—$CH_2$ group, if appropriate converting a resulting compound of the formula V into the open-chain hydroxycarboxylic acid of the formula V' or an ester or salt thereof, or if appropriate converting a salt or an ester into the free hydroxycarboxylic acid.

One or more of the optional measures can be carried out in any desired sequence in the process.

In the reaction with nucleophilic compounds $R^7AH$, the 4(R)-Michael addition products are formed stereospecifically under basic catalysis (see equation 1, V). The 4(S)-isomers of V have been formed only in very small amounts (<1 to 2%), if at all, in these addition reactions.

The process for the preparation of compounds V where $R^8$=structural element VI (equation 1, compound Va) or where $R^8$=structural element VII with X-Y=trans- CH=CH (equation 1, compound Vb) is illustrated in the following equation 1 with the aid of an example:

Equation 1:

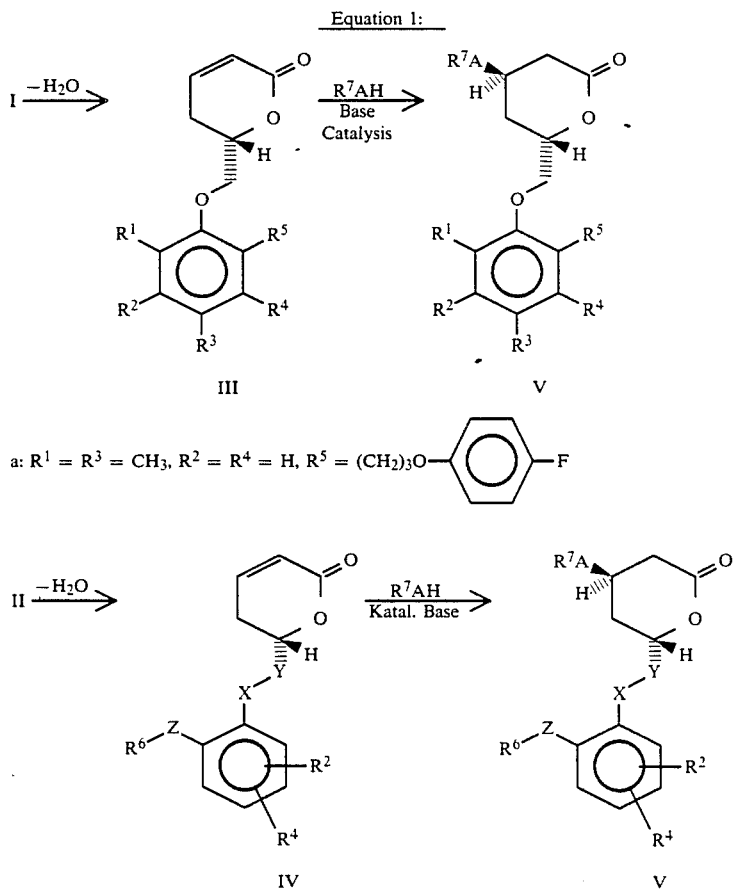

Equation 1:

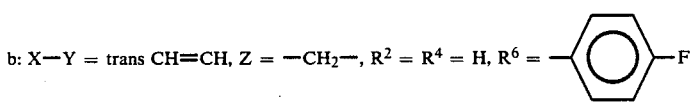

b: X—Y = trans CH=CH, Z = —CH$_2$—, R$^2$ = R$^4$ = H, R$^6$ =

10

The preparation of the optically pure starting compounds of the formulae I and II is described in German Patent Applications P 35 30 798.6 and P 35 43 336.1 (=U.S. patent application Ser. No. 900,848) and P 35 30 797.8 (=U.S. patent application Ser. No. 900,887).

The synthesis of compounds of the formula I or I' and conversion into the α,β-unsaturated lactones III is illustrated in the following equation 2 with the aid of an example.

Equation 2: Synthesis of III a

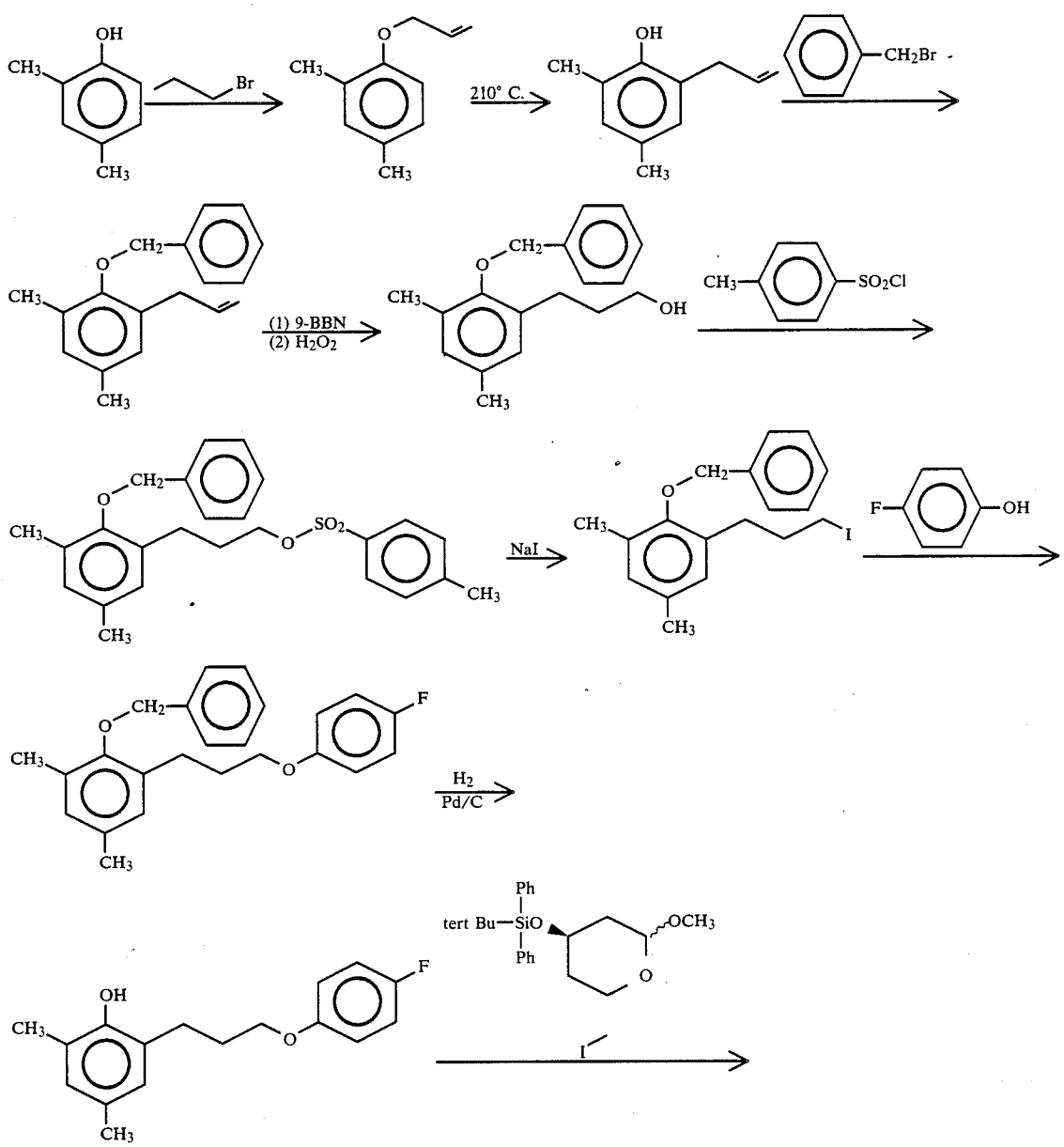

-continued
Equation 2: Synthesis of III a
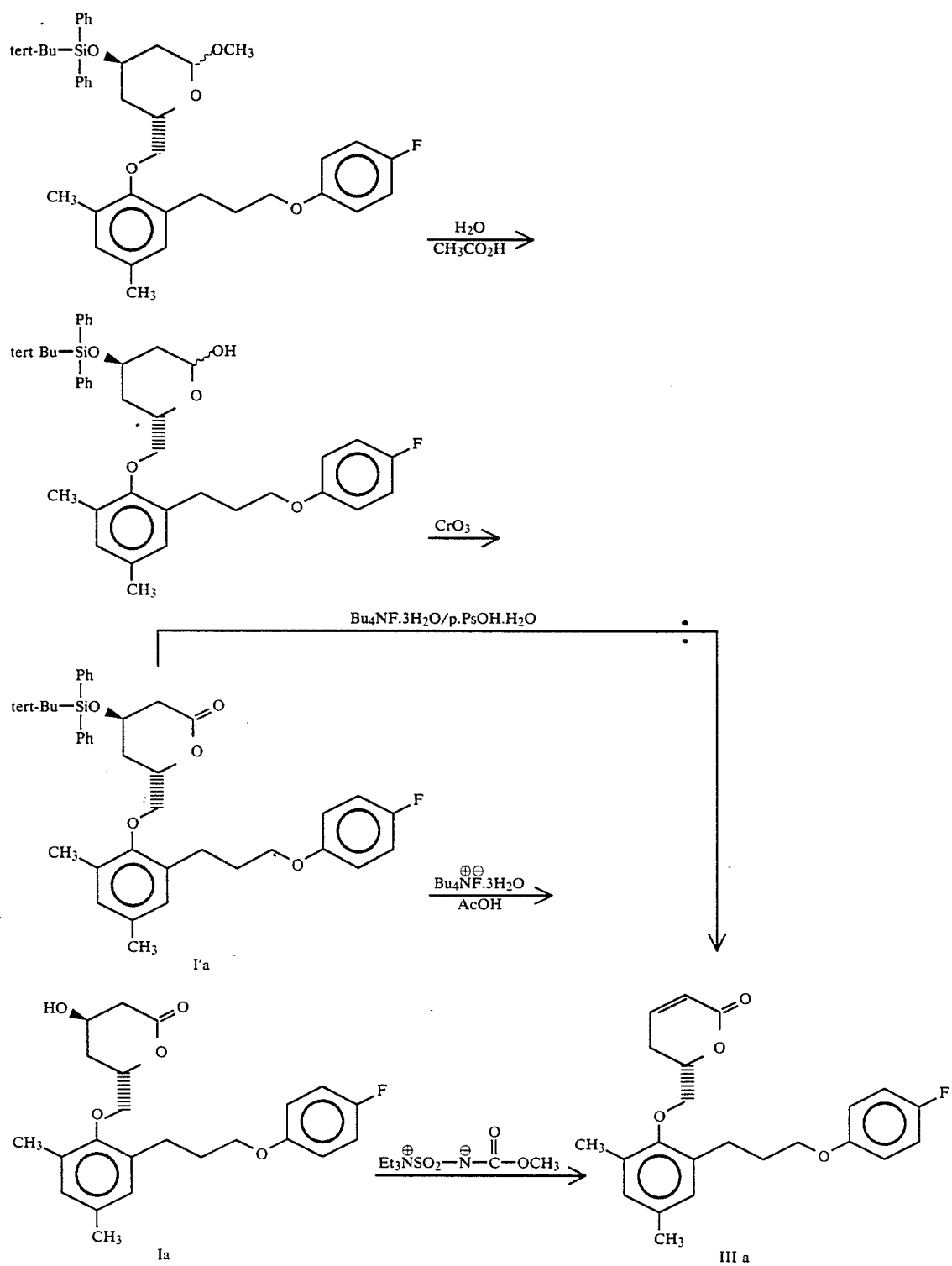
The preparation of the starting compounds II and conversion into the α,β-unsaturated lactones IV is illustrated in the following equation 3 with the aid of an example:

Equation 3: Synthesis of IV b

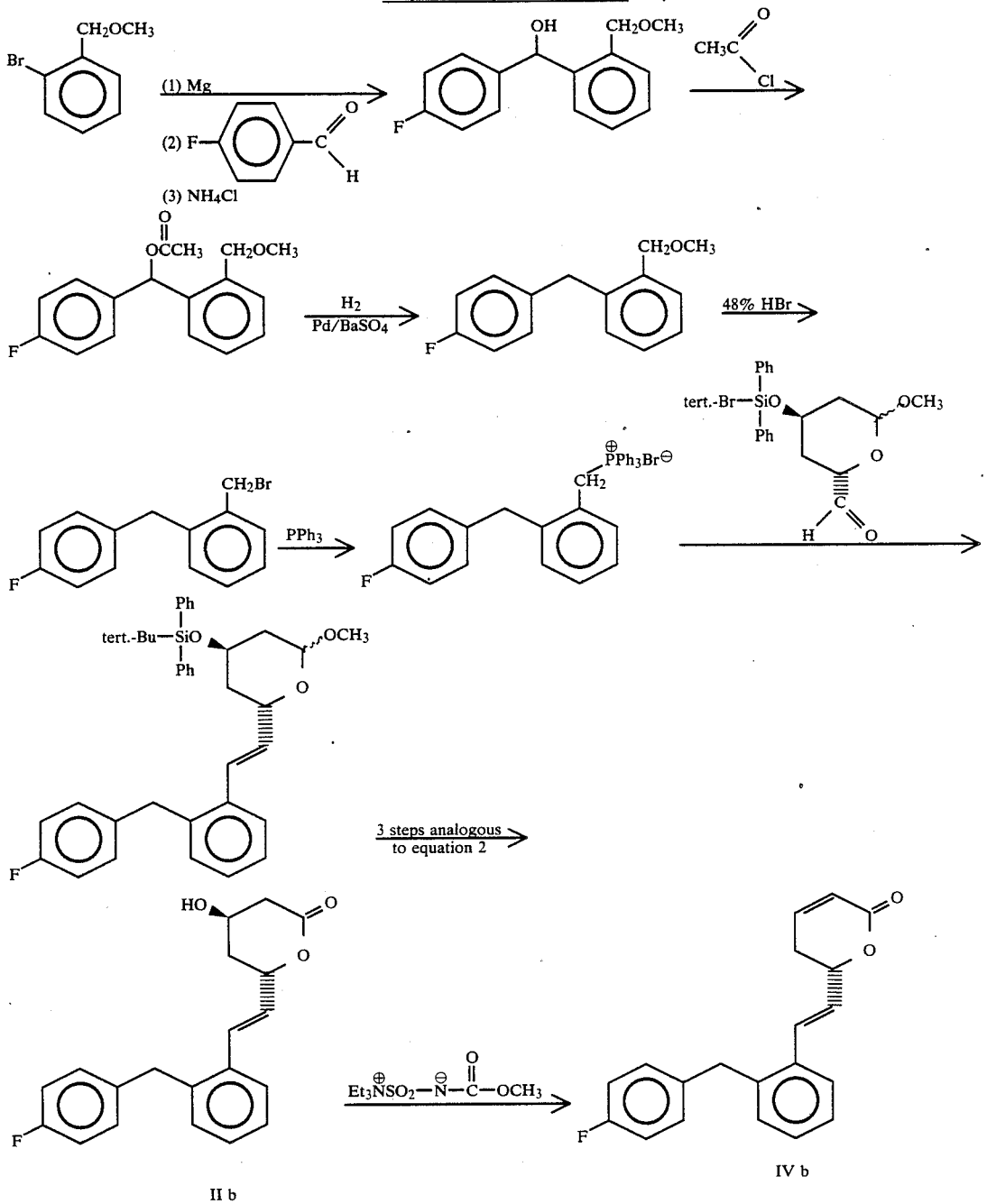

The removal of water from compounds of the formula I, compounds of the formula III being formed, such as, for example, from the compound Ia according to equation 2 to give compound IIIa, is advantageously carried out by warming with Burgess reagent (E. M. Burgess et al., J. Org. Chem. 38, 26 (1973)), but other customary methods are also suitable, such as phosphorus oxychloride/base, tosyl chloride or mesyl chloride/base or p-tolyl chlorothioformate (W. H. Rastetter et al., J. Org. Chem. 45, 3149 (1980)), sulfuran reagents (J. C. Martin et al., JACS 93, 4327 (1971) and JACS 94, 5003 (1972)), triphenylphosphine/carbon tetrachloride (R. Appel et al., Chem. Ber. 109, 3446 (1976)), methyltriphenoxyphosphonium iodide (C. W. Spangler et al., J. Chem. Soc. Perkin I, 2287 (1981)), warming in benzene or toluene under acid catalysis or warming in dimethylsulfoxide or hexamethylphosphoric acid triamide (R. S. Monson et al., J. Org. Chem. 36, 3827 (1971)) or warming with aluminum oxide (D. Dautzenberg et al., J. Org. Chem. 45, 3149 (1980)).

The removal of tert.-butyl-diphenylsilanol from I'a to give IIIa (equation 2) is carried out, for example, with tetrabutylammonium fluoride/para-toluenesulfonic acid already at room temperature.

The removal of water from compounds II, lactones IV being formed, such as, for example, from IIb to give IVb (equation 3) is advantageously carried out by warming with Burgess reagent (E. M. Burgess et al., J. Org. Chem. 38, 26 (1973)), but the abovementioned alternative methods are also suitable. This process is preferred for preparation of the lactones IV.

The reaction of the α,β-unsaturated lactones III or IV with nucleophilic compounds $R^7AH$ is carried out in the presence of basic catalysts, such as, for example, triethylamine, sodium hydride, sodium carbonate or sodium hydroxide. The reaction is carried out in the presence or absence of a solvent, such as, for example, ethanol or benzene, preferably at room temperature.

The ring opening to give compounds V' is carried out, for example, in an alkaline medium in the presence of sodium hydroxide.

Whilst the 4(R) addition products V are formed stereospecifically in the case of addition of, for example, thioacetic acid, benzylmercaptan, β-mercaptoethanol or L-cysteine, opening of the lactone ring to give the amide can additionally take place, alongside the desired addition reaction to give compounds V, in the case of addition of one equivalent of an amine, such as, for example, benzylamine. In such cases, it is advantageous to use an excess of amine and to prepare the double adducts, and to hydrolyze the amide to give the open-chain hydroxycarboxylic acid V'.

The α,β-unsaturated lactones of the formulae III to VI are novel. The invention therefore also relates to the compounds of the formulae III and IV and to processes for their preparation.

The enzyme HMG-CoA reductase is widespread in nature. It catalyzes the formation of mevalonic acid from HMG-CoA. This reaction is a central step in cholesterol biosynthesis (I. R. Sabine, 3-Hydroxy-3-methylglutaryl coenzyme A reductase, CRC Press, 1983). High cholesterol levels are associated with a number of diseases, such as, for example, coronary heart disease or atherosclerosis. The reduction of increased cholesterol levels is therefore a therapeutic aim for preventing and treating such diseases. One point of attack lies in inhibition or reduction of endogenous cholesterol synthesis. Inhibitors of HMG-CoA reductase block cholesterol biosynthesis at an early stage. They are therefore suitable for preventing and treating diseases caused by an increased cholesterol level. A reduction in the endogenous synthesis leads to an increased absorption of cholesterol from the plasma into the cells. An additional effect can be achieved by simultaneous administration of substances which bind bile acids, such as anion exchangers. The increased excretion of bile acids leads to intensified re-synthesis and therefore to an increased degradation of cholesterol (M. S. Brown, P. T. Kovanen, J. L. Goldstein, Science 212, 628 (1981); and M. S. Brown, J. L. Goldstein, Spektrum der Wissenschaft 1985, 96). The compounds according to the invention are inhibitors of HMG-CoA reductase. They are therefore suitable for inhibiting or preventing cholesterol biosynthesis and hence for preventing or treating diseases caused by increased cholesterol levels, in particular coronary heart disease, atherosclerosis, hypercholesterolaemia, hyperlipoproteinaemia and similar diseases.

The invention therefore also relates to pharmaceutical products based on the compounds of the formula V or the corresponding hydroxycarboxylic acids V' or salts and esters thereof, and to the use of these compounds as medicaments, in particular for the treatment of hypercholesterolaemia.

The compounds of the formula V or the corresponding acids, salts or esters are administered in various dosage forms, preferably orally in the form of tablets, capsules or liquids. The daily dose varies in the range from 3 mg to 2,500 mg, but preferably in the dose range from 10 to 500 mg, according to the body weight and constitution of the patient.

The compounds according to the invention can be used as lactones of the general formula V, in the form of the free acid V' or in the form of pharmaceutically acceptable salts or esters, and in particular as a solution or suspension in pharmacologically acceptable organic solvents, such as mono- or polyhydric alcohols, such as, for example, ethanol or glycerol, in triacetin, oils, such as, for example, sunflower oil or cod-liver oil, ethers, such as, for example, diethylene glycol dimethyl ether, or polyethers, such as, for example, polyethylene glycol, or also in the presence of other pharmacologically acceptable polymeric carriers, such as, for example, polyvinylpyrrolidone, or as a mixture with other pharmaceutically acceptable additives, such as starch, cyclodextrin or polysaccharides. The compounds according to the invention can furthermore be combined with additives which bind bile acid, in particular non-toxic basic anionic exchanger resins which bind bile acids in a nonabsorbable form in the gastrointestinal tract. The salts of the hydroxycarboxylic acids can also be processed as an aqueous solution.

The HMG-CoA reductase activity was determined on the following test system:

Inhibition of HMG-CoA Reductase Activity on Solubilized Enzyme Preparations From Rat Liver Microsomes The HMG-CoA reductase activity was measured on solubilized enzyme preparations from rat-liver microsomes which were induced with cholestyramine ($^R$Cuemid), after conversion to a day-night rhythm. (S,R) $^{14}$C-HMG-CoA was used as the substrate and the concentration of NADPH was maintained by a regenerating system during the incubation. The removal of $^{14}$C-mevalonate from the substrate and other products (for example $^{14}$-C-HMG) was effected via column elution, the elution profile of each individual sample being determined. Continuous simultaneous running of $^3$H-mevalonate was dispensed with, because the determination is a relative value of the inhibiting action. In each case the enzyme-free control, the enzyme-containing normal batch (=100%) and those with additions of the products were treated together in one experimental series. Each individual value was determined as a mean value from 3 parallel samples. The significance of the mean value differences between samples containing no product and samples containing product was evaluated by the t-test.

The following inhibiting values on HMG-CoA reductase were determined, for example, by the method described above for the compounds V according to the invention in comparison with the compounds A and B described in German Patent Application P 35 43 336.1 (=U.S. patent application Ser. No. 900,848) (A=6(S)-{4,6-dimethyl-2-[3-(4-fluorophenoxy)propyl]phenoxymethyl}-3,4,5,6-tetrahydro-4(R)-hydroxy-2H-pyran-2-one; B=sodium 3(R),5(S)-dihydroxy-6-{4,6-dimethyl-2-[3-(4-fluorophenoxy)propyl]phenoxy}hexanoate) [IC$_{50}$ value (mol/l) denotes the molar concentration of the compounds per liter which is required for 50% inhibition]:

| Compound | IC$_{50}$ value (mol/l) |
|---|---|
| A | $1.10^{-6}$ |
| B | $2.10^{-7}$ |
| Va (Example 4) | $3.10^{-7}$ |
| Vc (Example 6) | $\sim 10^{-4}$ |
| Vd (Example 8) | $1.10^{-6}$ |
| Ve (Example 9) | 24% inhibition at $10^{-7}$ |
|  | 37% inhibition at $10^{-6}$ |

EXAMPLES

All the $^1$H-NMR spectra (unless indicated otherwise) were recorded in CDCl$_3$ with a trace of tetramethylsilane as an internal standard.

PREPARATION OF α,β-UNSATURATED LACTONES III AND IV

EXAMPLE 1

6S-({[2-(4-Fluorophenoxy-3-propyl)]-4,6-dimethylphenoxy}methyl)-5,6-dihydro-2H-pyran-2-one (IIIa)

A solution of 482 mg (1.2 mmol) of the hydroxylactone 6(S)-{4,6-dimethyl-2-[3-(4-fluorophenoxy)propyl]-phenoxymethyl}-3,4,5,6-tetrahydro-4(R)-hydroxy-2H-pyran-2-one (cf. German Patent Application P 35 43 336.1 = U.S. patent application Ser. No. 900,848 and equation 2, Ia) in 10 ml of dry benzene was added dropwise to a solution of 429 mg (1.8 mmol) of Burgess reagent (E. M. Burgess et al., J. Org. Chem. 38, 26 (1973)) in 30 ml of benzene. The reaction mixture was warmed to an internal temperature of 50° C. for 60 minutes, whereupon a fine white solid precipitated. Since thin-layer chromatography control still indicated a little starting material, the mixture was cooled briefly with ice, a further 216 mg of Burgess reagent were added and the mixture was warmed at 60° C. for a further 30 minutes. 10 ml of water were added at room temperature, the mixture was stirred for 10 minutes and the benzene phase was separated off. The aqueous phase was extracted twice more with ether and the combined organic extracts were washed with saturated sodium chloride solution, dried over magnesium sulfate, filtered and concentrated. Chromatography over a little silica gel with 40% ethyl acetate/60% petroleum ether gave 426 mg (1.11 mol, 92% yield) of α,β-unsaturated lactone IIIa as a colorless solid, melting point 77° to 78° C. R$_f$(ethyl acetate/cyclohexane 1:1): Ia (0.28), IIIa (0.66)
MS (EI): C$_{23}$H$_{25}$O$_4$F, 384 (M+), 273 (M+

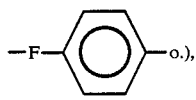

272 (M+

187, 135.

$^1$H-NMR (270 MHz): δ=2.0-2.12 (qui, 2H, CH$_2$), 216 (s, 3H, CH$_3$), 2.18 (s, 3H, CH$_3$), 240-2.57 (dtd, 1H; methylene-H), 2.67-2.80 (m, 3H), 3.92-4.00 (t, overlapped by d, 4H, methylene-H), 4.68-4.80 (d qua, 1H, CH), 6.04-6.10 (ddd, 1H, =C—H), 6.8-7.0 (m, 3H, =C—H and 2 aromatic-H).

EXAMPLE 2

6S-({[2-(4-Fluorophenoxy-3-propyl)]-4,6-dimethylphenoxy)}methyl)-5,6-dihydro-2H-pyran-2-one (IIIa)

190 mg (0.6 mmol) of tetrabutylammonium fluoride trihydrate and then 38 mg (0.2 mmol) of p-toluenesulfonic acid monohydrate were added to a solution of 128 mg (0.2 mmol) of the silyloxylactone 6(S)-{4,6-dimethyl-2-[3-(4-fluorophenoxy)propyl]phenoxymethyl}-3,4,5,6-tetrahydro-4(R)-(t-butyl-diphenylsilyloxy)-2H-pyran-2-one (cf. German Patent Application P 35 43 336.1 = U.S. patent application Ser. No. 900,848 and equation 2, I'a) in 7 ml of tetrahydrofuran. The mixture was stirred at room temperature for 12 hours and concentrated and the residue was chromatographed over silica gel with cyclohexane/ethyl acetate (1:1). 60.3 mg (0.157 mmol, 79% yield) of IIIa with physical and spectral data as in Example 1 were obtained.

EXAMPLE 3

6S-[2-(4-Fluorobenzyl)-E-styryl]-5,6-dihydro-2H-pyran-2-one (IVb)

200 mg (0.61 mmol) of the hydroxylactone (+)-E-6S-[2-(2-(4-fluorobenzyl)phenyl-ethenyl]-4R-hydroxy-3,4,5,6-tetrahydro-2H-pyran-2-one (cf. German Patent Application P 35 30 797.8 = U.S. patent application Ser. No. 900,887 and equation 3, IIb) and 365 mg (1.53 mmol) of Burgess reagent (E. M. Burgess et al., J. Org. Chem. 38, 26 (1973)) were dissolved in 20 ml of dry benzene. The solution was warmed at 60° C. under nitrogen for 2 hours. A further 182 mg of Burgess reagent were added at 25° C. and the mixture was then stirred at 60° C. for a further hour. Thin-layer chromatography (cyclohexane/ethyl acetate 1:1) indicated complete conversion to IVb [IIb (R$_f$=0.13), IVb (0.42)]. The solvent was removed in vacuo and the residue was subjected to flash chromatography over silica gel using the above mobile phase. 130 mg (0.42 mmol, 69% yield).

MS (EI) C$_{20}$H$_{17}$O$_2$F, 308 (M+), 223, 196.

$^1$H-NMR (270 MHz): δ=2.33-2.39 (m, 2H, CH$_2$), 3.96 (s, 2H, CH$_2$), 496 (qua with remote coupling, 1H, CH), 5.98 (dt, 1H, olefinic-H), 6.04 (dd, 1H, olefinic-H), 6.78-7.22 (m, 9H, 8 aromatic-H+1 olefinic-H), 7.40 (m, 1H, olefinic-H)

PREPARATION OF END PRODUCTS

EXAMPLE 4

6S-({[2-(4-Fluorophenoxy-3-propyl)]-4,6-dimethylphenoxy}methyl)-4R-acetylmercapto-3,4,5,6-tetrahydro-2H-pyran-2-one (Va, R$^8$=structural element VI)

36 μl (0.5 mmol) of thioacetic acid (freshly distilled) and then 7 μl of triethylamine were added to 115 mg (0.3 mmol) of the unsaturated lactone IIIa (Examples 1, 2). Thin-layer chromatography indicated complete reaction after 30 minutes (R$_f$ with 30% ethyl acetate/70% petroleum ether IIIa 0.39, Va 0.48, thioacetic acid 0.09). Filtration through a short silica gel column gave 130 mg (0.28 mmol, 94% yield) of adduct Va as a viscous colorless oil.

MS (FAB): C$_{25}$H$_{29}$SO$_5$F, 461 (M+H+), 348 (M+-F-C$_6$H$_4$-OH).

$^1$H-NMR (270 MHz): δ=2.0-2.1 (qui, 2H, CH$_2$), 2.1-2.2 (dt, 1H, methylene-H); 2.23 (s, 3H, CH$_3$), 2.26 (s, 3H, CH₃), 2.36 (s, 3H, CO-CH₃), 2.44–2.56 (m, 1H, methylene-H), 2.63–2.73 (ddd, 1H, methylene-H), 2.76 (t, 2H, CH₂), 2.90–3.01 (ddd, 1H, methylene-H), 3.88–4.0 (m, 4H, twice OCH₂), 4.15 (qui, 1H, CH), 4.77 (m, 1H, CH), 6.8–7.0 (m, 6H, aromatic-H).

EXAMPLE 5

6S-[2-(4-Fluorobenzyl)-E-styryl]-4R-acetylmercapto-3,4,5,6-tetrahydro-2H-pyran-2-one (Vb, R⁸=structural element VII)

A solution of 56 μl (0.78 mmol) of thioacetic acid in 1 ml of toluene and then 27 μl (0.19 mmol) of triethylamine were added to a solution of 120 mg (0.39 mmol) of the unsaturated lactone IV b (Example 3) in 5 ml of toluene. After one hour, the solvent was removed and the residue was purified over silica gel using cyclohexane/ethyl acetate (8:2). 121 mg (0.31 mmol, 81% yield) of Vb were obtained as an oil.

$R_f$ (cyclohexane/ethyl acetate 1:1): IVb (0.38), Vb (0.47)

MS (EI): C₂₂H₂₁O₃SF 384 (M⁺), 341 (M⁺—CH₃—C═O), 308 (M⁺

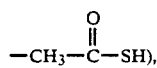

197, 109 (F-C₆H₄-CH₂⁺).

¹H-NMR (270 MHz): δ=2.0–2.2 (m, 2H, CH₂), 2.37 (s, 3H, CH₃), 2.61 (dd, 1H, methylene-H), 2.87 (dd, 1H, methylene-H), 3.86 (qui, 1H, CH), 4.03 (s, [very narrow AB system], 2H, CH₂), 5.12 (m, 1H, olefinic-H), 6.85 (dd, 1H, olefinic-H), 6.9–7.0 (m, 2H, aromatic-H), 7.01–7.07 (m, 2H, aromatic-H), 7.12–7.17 (m, 1H, aromatic-H), 7.23–7.29 (m, 2H, aromatic-H), 7.43–7.49 (m, 1H, aromatic-H).

EXAMPLE 6

6S-({[2-(4-Fluorophenoxy-3-propyl)]-4,6-dimethylphenoxy}methyl)-4R-benzylmercapto-3,4,5,6-tetrahydro-2H-pyran-2-one (Vc, R⁸=structural element VI)

59 μl (0.5 mmol) of benzylmercaptan (freshly distilled) and then 14 μl (0.1 mmol) of dry triethylamine were added to 77 mg (0.2 mmol) of the unsaturated lactone IIIa (Examples 1, 2). Analysis by thin-layer chromatography after 1 hour indicated almost complete reaction. After the mixture had been left to stand overnight at 0° C. under nitrogen, the reaction was complete. $R_f$ with 20% ethyl acetate/80% cyclohexane IIIa 0.19, Vc 0.39, benzylmercaptan 0.82. The oil was subjected to flash chromatography directly over a short silica gel column. 96.5 mg (0.19 mmol, 96% yield) of Vc were obtained as a viscous colorless oil.

MS (EI) C₃₀H₃₂SO₄F, 508 (M⁺), 396 (M⁺-F-C₆H₄-OH), 384 (M⁺-C₆H₅SH).

¹H-NMR (270 MHz): δ=1.98–2.1 (m, 2H, CH₂ and 1 methylene-H), 2.23 (s, 3H, CH₃), 2.25 (s, 3H, CH₃), 2.25–2.36 (m, 1H, methylene-H), 2.56–2.66 (ddd, 1H, methylene-H), 2.73 (t, 2H, CH₂), 2.77–2.87 (dd, 1H, methylene-H), 3.27 (qui, 1H, CH), 3.78 (narrow AB system, 2H, SCH₂), 3.87 (t, 2H, OCH₂), 3.94 (t, 2H, OCH₂), 4.85 (m, 1H, CH), 6.79–6.87 (m, 4H, aromatic-H), 6.9–7.0 (m, 2H, aromatic-H), 7.28–7.35 (m, aromatic-H).

EXAMPLE 7

Sodium 6-{[2-(4-fluorophenoxy-3-propyl)]-4,6-dimethylphenoxy}-3R-benzylmercapto-5S-hydroxy-hexanoate (V'c, Na salt R⁸=structural element VI)

74 mg (0.145 mmol) of Vc (Example 6) were dissolved in 5 ml of ethanol, and 1.37 ml of 0.1N sodium hydroxide solution were added. After 2 hours, the mixture was concentrated to dryness in vacuo. The residue was concentrated to dryness in vacuo. The residue was digested twice with ether. The salt V'c was dried in vacuo; 69.4 mg (0.127 mmol, 88% yield).

¹H-NMR (D₂O, 270 MHz, reference point HOD δ=4.80): δ=1.2–1.56 (dt, 1H, methylene-H), 1.55–1.85 (m, 2H, CH₂), 1.91 (s, 3H, CH₃), 2.01 (s, 3H, CH₃), 2.3–2.65 (m, 4H, 2CH₂), 3.0–3.45 (m, 3H), 3.45–3.6 (m, 4H), 3.96–4.11 (broad, 1H, CH), 6.46, 6.63 (m, 4H, aromatic-H), 6.65–6.80 (m, 2H, aromatic-H), 6.85–6.92 (m, 1H, aromatic-H), 6.93–7.00 (t, 2H, aromatic-H), 7.02–7.11 (t, 2H, aromatic-H).

EXAMPLE 8

6S-({[2-(4-Fluorophenoxy-3-propyl)]-4,6-dimethylphenoxy}methyl)-4R-β-hydroxyethylmercapto-3,4,5,6-tetrahydro-2H-pyran-2-one (Vd, R⁸=structural element VI)

30 μl (0.43 mmol) of mercaptoethanol and then 14 μl (0.1 mmol) of triethylamine were added to 87 mg (0.2227 mmol) of the unsaturated lactone IIIa (Examples 1, 2). Thin-layer chromatography indicated complete reaction after one hour. The oil was subjected to flash chromatography directly over a short silica gel column using 50% ethyl acetate/50% petroleum ether. Excess mercaptoethanol is eluted before the product Vd (63.1 mg, 0.136 mmol, 60% yield, oil).

MS (EI) C₂₅H₃₁SO₅F, 462 (M⁺), 384 (M⁺-HOCH₂CH₂SH), 350 (M⁺-FC₆H₄-OH).

¹H-NMR (270 MHz) δ=1.76 (s, 1H, OH), 2.0–2.1 (qui, 2H, CH₂), 2.13–2.2 (t, 1H, methylene-H), 2.23 (s, 3H, CH₃), 2.25 (s, 3H, CH₃), 2.38–2.50 (m, 1H, methylene-H), 2.59–2.70 (ddd, 1H, methylene-H), 2.71–2.80 (m, 4H, twice CH₂), 2.88–2.97 (dd, 1H, methylene-H), 3.48–3.57 (qui, 1H, CH), 3.78 (t, 2H, CH₂), 3.9–4.0 (m, 4H, 2 OCH₂), 4.85–4.94 (m, 1H, CH), 6.8–6.9 (m, 4H, aromatic-H), 6.92–7.0 (m, 2H, aromatic-H).

EXAMPLE 9

6S-({[2-(4-Fluorophenoxy-3-propyl)]-4,6-dimethylphenoxy}methyl)-4R-[(R)-2-amino-3-mercaptyl-propionic acid]-3,4,5,6-tetrahydro-2H-pyran-2-one (Ve, R⁸=structural element VI)

A mixture of 77 mg (0.2 mmol) of the unsaturated lactone IIIa (Examples 1, 2), 32 mg (0.3 mmol) of sodium carbonate and 62 mg (0.4 mmol) of L-cysteine hydrochloride was dissolved in 1 ml of absolute ethanol at 25° C. Thin-layer chromatography after one hour indicated no reaction. 50 μl (0.36 mmol) of triethylamine were added, whereupon a colorless precipitate immediately formed. The solvent was stripped off and the residue was dissolved in the minimum amount of chloroform/methanol (7:3). The crude product was chromatographed through silica gel (φ2.5 cm, height 13 cm) using methylene chloride/methanol (7:3). 98.3 mg (0.195 mmol, 97% yield) of Ve were obtained as a colorless powder, melting point (without recrystallization)

175°–176° C. (with decomposition, yellow coloration, gases)

MS (FAB, NBA matrix): $C_{26}H_{32}NO_6SF$ 574 $(M+Na_3^+)$, 550 $(M+Na_2^+ - H^+)$, 528 $(M+Na^+)$, 506 $(M+H^+)$, 407 $(M+Na^+ - F-C_6H_4O.)$.

IR (KBr): 3600–3300 cm$^{-1}$ (broad, $NH_2$), 3300–3000 (broad, $—NH_3^+$), 3000–2400 (very broad, $CO_2H$), 1740 (C=O of the lactone), 1510 (aromatic)

$^1$H-NMR (DMSO-d$_6$, 270 MHz) $\delta$=1.9–2.0 (qui, 2H, $CH_2$), 2.08 (dt, 1H, methylene-H), 2.18 (s, 3H, $CH_3$), 2.20 (s, 3H, $CH_3$), 2.28 (dt, 1H, methylene-H), 2.56 (dd, 1H, S-CH), 2.70 (t, 2H, $CH_2$), 2.86 (dd, 1H, methylene-H), 2.92 (dd, 1H, S-CH), 3.11 (dd, 1H, methylene-H), 3.2–3.5 (broad, 3H, $NH_3^+$), 3.37 (qui, 1H, CH), 3.56 (qui, 1H, CH), 3.85–3.9 (m, 2H, $OCH_2$), 3.96 (t, 2H, $OCH_2$), 4.83–4.92 (m, 1H, CH), 6.83 (s, 2H, aromatic-H), 6.9–6.97 (m, 2H, aromatic-H), 7.07–7.15 (m, 2H, aromatic-H).

EXAMPLE 10

Sodium 6-{[2-(4-fluorophenoxy-3-propyl)]-4,6-dimethylphenoxy}-3R-[(R)-2-amino-3-mercaptyl-sodium propionate]-5S-hydroxy-hexanoate (V'e, Na salt $R^8$=structural element VI)

200 g (0.393 mmol) of Ve (Example 9) were suspended in 10 ml of absolute ethanol. 3.93 ml of 0.1N sodium hydroxide solution were added, and after 10 minutes a further 3.73 ml of 0.1N NaOH were added. After 30 minutes, the solvent was stripped off. The residue was washed with 3 portions of 3 ml of ethanol and dried in vacuo. Yield 92 mg of V'e.

$^1$H-NMR (D$_2$O, 270 MHz, reference point HOD $\delta$=4.80): $\delta$=1.75–1.95 (m, 2H, $CH_2$), 2.0–2.12 (qui, 2H, $CH_2$), 2.22 (s, 3H, $CH_3$), 2.26 (s, 3H, $CH_3$), 2.32 (dd, 1H, S-CH), 2.59 (dd, 1H, S-CH), 2.69–2.83 (m, 3H, $CH_2$ and 1 methylene-H), 2.9–3.0 (m, 1H, methylene-H), 3.15–3.25 (m, 1H, methylene-H), 3.36 (s, 5H, OH, $NH_3^+$, $CO_2H$), 3.42 (dd, 1H, CH), 3.78 (d, 2H, $OCH_2$), 4.05 (t, 2H, $OCH_2$), 4.15 (m, 1H, CH), 6.9–7.0 (m, 4H, aromatic-H), 7.05–7.12 (t, 2H, aromatic-H).

EXAMPLE 11

Sodium 6-{[2-(4-fluorophenoxy-3-propyl)]-4,6-dimethylphenoxy}-3R-$\beta$-hydroxyethylamino-5S-hydroxy-hexanoate (V'f, Na salt $R^8$=structural element VI)

(a) 200 $\mu$l of dry dimethoxyethane and 180 $\mu$l (3.5 mmol) of ethanolamine were added to 128 mg (0.3 mmol) of the unsaturated lactone IIIa (Examples 1, 2). The reaction had ended after 1 hour at 25° C.

R$_f$ with 70% chloroform/30% methanol: IIIa 0.78, V'f-ethanolamide 0.15. The reaction mixture was filtered over a short silica gel column using the same eluting agent. 139 mg of V'f-ethanolamide (0.275 mmol, 91% yield) were obtained as a pale yellow oil.

MS (FAB, 3-NBA matrix) $C_{27}H_{39}FN_2O_6$ 507 $(M+H^+)$ MS (EI): 506 (M$^+$, very weak), 487 (M$^+$-H$_2$O-H.), 475 (M$^+$-.CH$_2$OH), 445 (M$^+$-HOCH$_2$CH$_2$NH$_2$), 427 ("445"-H$_2$O), 414 ("475"-HOCH$_2$CH$_2$NH$_2$), 384 (M$^+$-2HOCH$_2$CH$_2$NH$_2$), 316 ("427"-F-C$_6$H$_4$O.), 274 (M$^+$-F-C$_6$H$_4$OH-2 NHCH$_2$CH$_2$OH).

$^1$H-NMR (270 MHz) $\delta$=1.6–1.8 (m, 2H, CH$_2$), 2.4 (qui, 2H, CH$_2$), 2.22 (s, 6H, 2×CH$_3$), 2.33 (dd, 1H, methylene-H), 2.52 (dd, 1H, methylene-H), 2.7–3.1 (m, 7H, 2×CH$_2$, 2×OH, amine-H), 3.25–3.5 (m, 3H, OCH$_2$, CH), 3.6–3.8 (m, 6H, 3×CH$_2$), 3.92 (t, 2H, OCH$_2$), 4.18 (m, 1H, CH), 6.8–6.9 (m, 4H, aromatic-H), 6.9–7.0 (t, 2H, aromatic-H), 7.48 (t, 1H, amide-H)

(b) A solution of 55 mg (0.11 mmol) of V'f-ethanolamide and 427 mg (10.6 mmol) of NaOH in 1.1 ml of water and 1 ml of ethanol was boiled under reflux for 3 hours. After cooling, 5.2 ml of 2N hydrochloric acid were added ($\rightarrow$pH 8–9) and the mixture was concentrated to dryness in vacuo.

R$_f$ with 50% chloroform/50% methanol: V'f-ethanolamide 0.16, V'f (as carboxylic acid) 0.34

EXAMPLE 12

Sodium 6-{[2-(4-fluorophenoxy-3-propyl)]-4,6-dimethylphenoxy}-3R-benzylamino-5S-hydroxy-hexanoate (V'g, Na salt, $R^8$=structural element VI)

(a) 44 $\mu$l (0.4 mmol) of freshly distilled benzylamine and 100 $\mu$l of benzene were added to 77 mg (0.2 mmol) of the unsaturated lactone IIIa (Examples 1, 2). The reaction solution was warmed at 50°–60° C. for 12 hours (a further 200 $\mu$l of benzene were added after 6 hours). Flash chromatography through silica gel ($\phi$4 cm, height 10 cm) using 1 l of 75% ethyl acetate/25% petroleum ether and then using 99% ethyl acetate/1% triethylamine gave, after first runnings, the pure product V'g-benzylamide (marked tailing, 119 mg, 0.1999 mmol, 99% yield) as a viscous yellowish oil.

R$_f$ (100% ethyl acetate): IIIa 0.9, V'g-benzylamide 0.44.

MS (FAB, NBA matrix); $C_{37}H_{43}N_2O_4F$ 599 $(M+H^+)$, 450 $(M+H^+ - F-C_6H_4-OH-2H_2O)$.

IR (CHCl$_3$): 3600–3100 cm$^{-1}$ (OH and NH), 1645/1550 (amide), 1506 (aryl), 1210.

$^1$H-NMR (270 MHz) $\delta$=1.65–1.76 (m, 2H, CH$_2$), 2.03 (qui, 2H, CH$_2$), 2.23 (s, 6H, 2×CH$_3$), 2.34 (dd, 1H, methylene-H), 2.59 (dd, 1H, methylene-H), 2.7–2.8 (m, 2H, CH$_2$), 3.30 (sext., 1H, CH), 3.65 (d, 2H, NCH$_2$), 3.74 (d, 1H, NCH$_2$), 3.90 (dd, 1H, NCH$_2$), 3.90 (t, 2H, OCH$_2$), 4.1–4.2 (m, 1H, CH), 4.42 (AB section of ABX, 2H, OCH$_2$), 6.77–6.92 (m, 6H, aromatic-H) 7.2–7.35 (m, 12H, 10 aromatic-H and 2 NH).

(b) Hydrolysis of the benzylamide of V'g was carried out in a manner analogous to that described in Example 11. The sodium salt V'g was obtained.

EXAMPLE 13

6S-({[2-(4-Fluorophenoxy-3-propyl)]-4,6-dimethylphenoxy}methyl)-4R-[(bis-ethoxycarbonyl)-methyl]-3,4,5,6-tetrahydro-2H-pyran-2-one (Vh, $R^8$=structural element VI)

The sodium hydride which remains after 2 washing/decanting operations on 20 mg of 55–60% strength NaH suspension in oil with pentane is added to a solution of 115.2 mg (0.3 mmol) of IIIa (Examples 1, 2) and 58.6 mg (0.36 mmol) of diethyl malonate. The reaction mixture is stirred at room temperature for 2 hours. It is purified by means of filtration through silica gel with cyclohexane/ethyl acetate (2:1).

R$_f$(cyclohexane/ethyl acetate 3:2): Vh 0.49, impurity (Vh stereoisomer) 0.42, IIIa 0.32.

115 mg (0.21 mmol, 70% yield) of Vh are obtained as a colorless oil.

MS (EI); $C_{30}H_{37}FO_8$, 544 (M$^+$), 499 (M$^+$-OCH$_2$CH$_3$), 432 (M$^+$-F-C$_6$H$_4$OH), 387 ("432"-OCH$_2$CH$_3$), 271.

$^1$H-NMR (270 MHz) δ=1.25 (t, 3H, ester, CH$_3$), 1.30 (t, 3H, ester, CH$_3$), 1.82 (qua, 1H, CH), 2.05 (qui, 2H, CH$_2$), 2.24 (s, 6H, 2×CH$_3$), 2.25–2.40 (m, 2H, one methylene-H twice), 2.48 (dd, 1H, methylene-H), 2.75 (t, 2H, CH$_2$), 3.32 (d, 1H, CH), 3.88–4.0 (m, 4H, 2×OCH$_2$), 4.20 (qua, 2H, ester-CH$_2$), 4.26 (qua, 2H, ester-CH$_2$), 4.7 (m, 1H, CH), 6.8–6.88 (m, 4H, aromatic-H), 6.9–7.0 (t, 2H, aromatic-H).

EXAMPLE 14

Sodium 6-{[2-(4-fluorophenoxy-3-propyl)]-4,6-dimethylphenoxy}-3R-[(bis-sodiumcarboxyl)-methyl]-5S-hydroxyhexanoate (V'h, Na salt R$^8$=structural element VI)

61 mg of Vh (0.112 mmol) were dissolved in 3 ml of ethanol/5 drops of chloroform, and 3.36 ml (3 equivalents) of 0.1N sodium hydroxide solution were added. After stirring for 6 hours, the volatile constituents were stripped off and the residue was concentrated under a high vacuum twice with toluene. Thin-layer chromatography indicated complete hydrolysis to V'h.

We claim:

1. A 4(R)-substituted 6(S)-phenyloxymethyl-, 6(S)-β-phenylethyl- and 6(S)-β-styryl-tetrahydropyran-2-one of the formula V

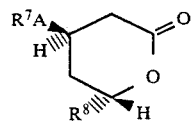

in which:
A is —S—
R$^7$
  (a) is a straight-chain or branched alkyl group which has 1–3 carbon atoms and which is unsubstituted or is substituted
    (aa) by a hydroxyl group
    (ab) by an amino or ammonium group
    (ac) by a carboxyl group CO$_2$H or the methyl, ethyl or benzyl ester or methyl- or dimethylamide or sodium, potassium or ammonium salt thereof
    (ad) by a phenyl group
    (ae) by 1 to 3 halogen atoms
  (b) is an alkanoyl group

in which R$^9$ is a straight-chain or branched alkyl group which has 1 to 4 carbon atoms and is unsubstituted or is substituted by the groups recited under (aa) or (ae)
  (c) is a carboxyl group, the methyl, ethyl or benzyl ester, or methyl- or dimethylamide, or sodium, potassium or ammonium salt thereof, or
  (d) is hydrogen R$^8$ represents the structural elements of the formulae VI or VII

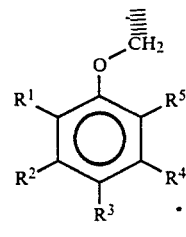

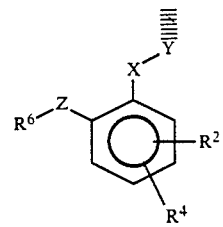

in which
X-Y is a group of the formula trans —CH=CH— or —CH$_2$—CH$_2$—
Z is a —CH$_2$— or —CH$_2$—CH$_2$— group
R$^1$ and R$^5$ are identical or different and
  (a) are hydrogen or halogen
  (b) are cycloalkyl with 4 to 8 carbon atoms or a phenyl group, which is unsubstituted or is mono-, di- or tri- substituted in the nucleus by at least one substituent selected from the group consisting of halogen, trifluoromethyl, alkyl and alkoxy, said alkyl or alkoxy having 1 to 4 carbon atoms, or
  (c) is a straight-chain or branched alkyl group with 1 to 18 carbon atoms, a straight-chain or branched alkenyl group with 2 to 18 carbon atoms, said alkyl and alkenyl groups being unsubstituted or mono-, di- or trisubstituted by
    (i) a straight-chain or branched alkoxy group with up to 10 carbon atoms, a cycloalkoxy group with 3 to 7 carbon atoms, or a straight-chain or branched alkenyloxy or alkynyloxy group with 3 to 6 carbon atoms
    (ii) halogen, hydroxyl, cycloalkyl with 3 to 7 carbon atoms, unsubstituted phenyl or α- or β-thienyl groups or phenyl or α- or β-thienyl groups which are mono-, di- or trisubstituted in the nucleus by at least one substituent selected from the group consisting of halogen, trifluoromethyl, alkyl and alkoxy, said alkyl or alkoxy having 1 to 4 carbon atoms,
    (iii) unsubstituted phenoxy, benzyloxy or α- or β-thienyloxy groups, or phenoxy, benzyloxy or α- or β-thienyloxy groups which are mono-, di- or trisubstituted in the nucleus by at least one substituent selected from the group consisting of halogen, trifluoromethyl, alkyl and alkoxy, said alkyl or alkoxy having 1 to 4 carbon atoms,
    (iv) the group

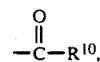

in which R$^{10}$ is a straight-chain or branched alkyl or alkenyl group with up to 8 carbon atoms, or a cycloalkyl or cycloalkenyl group each having 3 to 8 carbon atoms, or a phenyl group which is unsubstituted or is mono-, di- or trisubstituted in the nucleus by at least one substituent selected from the group consisting of halogen, trifluoromethyl, alkyl, alkoxy and a pyridyl group, said alkyl or alkoxy having 1 to 4 carbon atoms $R^2$ and $R^4$ are identical or different and are hydrogen, alkyl with 1 to 4 carbon atoms, halogen or alkoxy with 1 to 4 carbon atoms, and $R^3$ is hydrogen, alkyl or alkenyl with up to 4 carbon atoms, halogen or alkoxy with 1 to 4 carbon atoms, and $R^6$ is a cycloaliphatic hydrocarbon group with 3 to 7 carbon atoms, a phenyl group which is unsubstituted or is mono-, di- or trisubstituted in the nucleus by at least one substituent selected from the group consisting of halogen, trifluoromethyl, alkyl, alkoxy, said alkyl or alkoxy having 1 to 6 carbon atoms, and hydroxymethyl, a furyl, thienyl or pyridyl group, or said furyl, thienyl or pyridyl group which is mono- or disubstituted by at least one substituent selected from the group consisting of halogen, trifluoromethyl, alkyl and alkoxy, said alkyl or alkoxy having 1 to 6 carbon atoms, or a pharmacologically acceptable salt thereof with a base.

2. A compound as claimed in claim 1, in which, in the formula V,

A is —S—

$R^7$ (a) is a straight-chain or branched alkyl group which has 1 or 2 carbon atoms and is unsubstituted or is substituted by
 (aa) a hydroxyl group
 (ab) an amino or ammonium group
 (ac) a carboxyl group, or the methyl, ethyl or benzyl ester, or methyl- or dimethylamide, or sodium, potassium or ammonium salt thereof
 (ad) a phenyl group
 (ae) a fluorine or chlorine atom
(b) is an alkanoyl group

in which $R^9$ is a methyl or ethyl group which is unsubstituted or is substituted by one hydroxyl group or 1 to 3 fluorine atoms
(c) is a carboxyl group, or the methyl or ethyl ester, or methyl- or dimethylamide, or sodium, potassium or ammonium salt thereof, or
(d) is hydrogen $R^8$ represents the structural elements of the formulae VI or VII

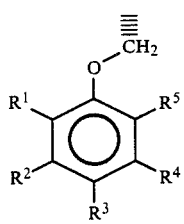

VI or

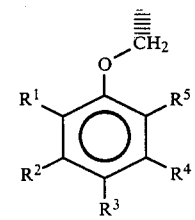

VII in which

X-Y is a group of the formula trans —CH=CH—, and

Z is a $CH_2$ group, $R^1$ and $R^5$ are identical or different and
 (a) is hydrogen or chlorine, or
 (b) is a straight-chain or branched alkyl group with 1 to 6 carbon atoms which is unsubstituted or is mono- or disubstituted by unsubstituted phenyl or phenoxy groups, or said phenyl or phenoxy groups substituted in the nucleus by fluorine or chlorine $R^2$ and $R^4$ are identical or different and are hydrogen, methyl, ethyl, fluorine or chlorine, $R^3$ is hydrogen, methyl or chlorine, and $R^6$ is a cycloalphatic hydrocarbon group with 5 to 6 carbon atoms or a phenyl group which is unsubstituted or is substituted in the nucleus by fluorine, chlorine, trifluoromethyl, methyl, ethyl, methoxy or ethoxy.

3. A compound as claimed in claim 1, in which, in the formula V,

A is —S—

$R^7$ (a) is an alkyl group which has 1 or 2 carbon atoms and is unsubstituted or is substituted by
 (aa) a hydroxyl group
 (ab) an amino or ammonium group
 (ac) a carboxyl group, or the methyl ester, or sodium, potassium or ammonium salt thereof
 (ad) a phenyl group
 (ae) a fluorine atom, or
(b) is an acetyl or trifluoroacetyl group $R^8$ represents the structural elements of the formulae VI or VII

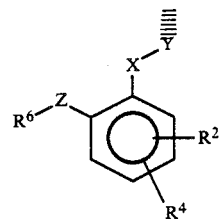

VI or

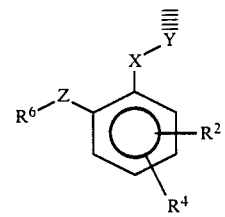

VII in which

X-Y is a group of the formula trans —CH=CH— and

Z is a —CH$_2$— group,

R$^1$ and R$^5$ are identical or different and (a) are chlorine, or (b) are a straight-chain or branched alkyl radical with 1 to 3 carbon atoms which is unsubstituted or is mono- or disubstituted by an unsubstituted phenyl or phenoxy group, or said phenyl or phenoxy group substituted in the nucleus by fluorine, and R$^2$ and R$^4$ are hydrogen R$^3$ is chlorine or methyl and R$^6$ is cyclohexyl or a phenyl group which is unsubstituted or is substituted by chlorine or fluorine.

4. A pharmaceutical composition for treating diseases caused by increased cholesterol levels in a host which comprises an effective amount of a compound of the formula V as claimed in claim 1 or a pharmaceutically acceptable salt thereof with a pharmaceutically acceptable carrier.

5. A method for the prophylaxis and therapy of hypercholesterolemia which comprises administering to a host in need of said prophylaxis and therapy, an effective amount of the formula V as claimed in claim 1.

* * * * *

UNITED STATES PATENT AND TRADEMARK OFFICE
CERTIFICATE OF CORRECTION

PATENT NO.  : 4,946,852

DATED       : August 7, 1990

INVENTOR(S) : Heiner Jendralla, et al.

It is certified that error appears in the above-identified patent and that said Letters Patent is hereby corrected as shown below:

On the title page, item [54] and in column 1, line 2, "PHENYLENTHYL" should be --PHENYLETHYL--.

Signed and Sealed this

Thirtieth Day of June, 1992

Attest:

DOUGLAS B. COMER

Attesting Officer

Acting Commissioner of Patents and Trademarks